(12) United States Patent
Wong

(10) Patent No.: US 7,123,958 B1
(45) Date of Patent: Oct. 17, 2006

(54) METHODS AND DEVICES FOR REDUCING INTEGRATED CIRCUIT POWER CONSUMPTION IN IMPLANTABLE CARDIAC STIMULATION DEVICES

(75) Inventor: Louis Wong, Santa Clara, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 692 days.

(21) Appl. No.: 10/011,018

(22) Filed: Dec. 4, 2001

(51) Int. Cl.
*A61N 1/362* (2006.01)

(52) U.S. Cl. .......................................................... 607/4
(58) Field of Classification Search .................. 607/4, 607/5, 9, 34, 11, 2, 29, 16; 322/28
See application file for complete search history.

(56) References Cited

U.S. PATENT DOCUMENTS

| | | | | |
|---|---|---|---|---|
| 3,656,050 A | * | 4/1972 | Airey | .......................... 322/28 |
| 6,091,987 A | | 7/2000 | Thompson | ....................... 607/2 |
| 6,185,454 B1 | * | 2/2001 | Thompson | ....................... 607/2 |
| 6,353,760 B1 | * | 3/2002 | Lyden | .......................... 607/11 |

* cited by examiner

*Primary Examiner*—George Manuel
(74) *Attorney, Agent, or Firm*—Steven M. Mitchell

(57) ABSTRACT

A voltage step-down circuit reduces the amount of power drawn from the battery of an implantable cardiac stimulation device (ICD) to supply an integrated circuit (IC) within the ICD. The ICD battery supply voltage is reduced to a level that maintains proper operation of the IC. The reduced battery supply voltage is also regulated such that the IC is supplied with a constant voltage source. The IC consumes less power when supplied by the reduced battery supply voltage than when supplied directly by the battery supply voltage. The present invention promotes ICD battery longevity and reduces the need for frequent ICD battery replacements.

30 Claims, 5 Drawing Sheets

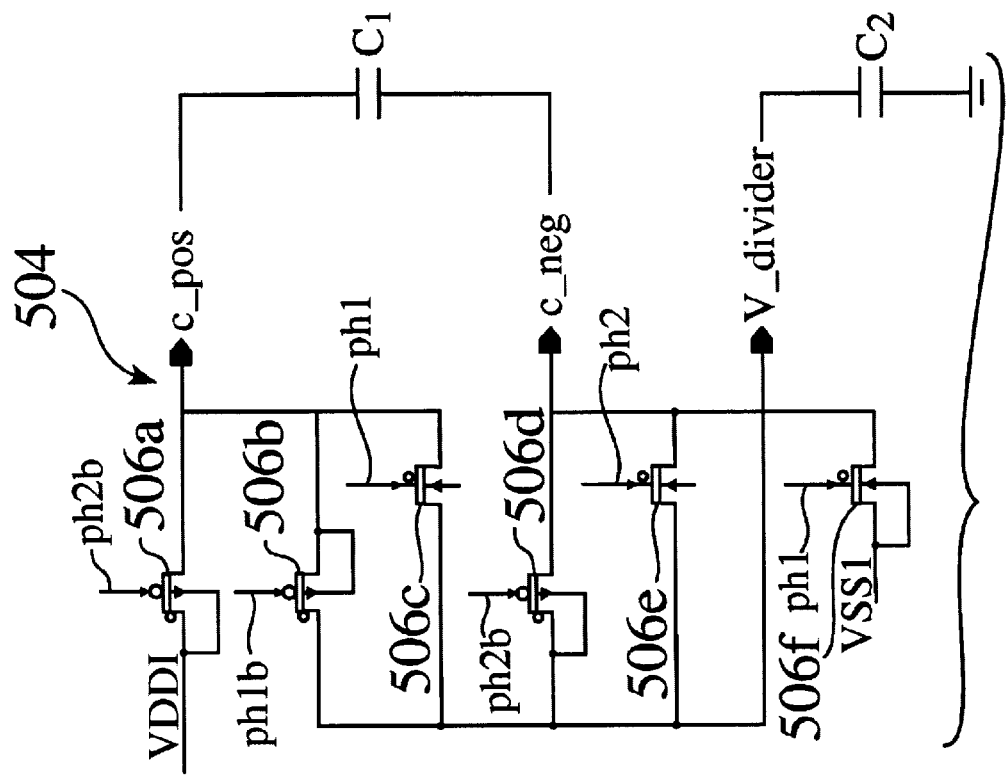
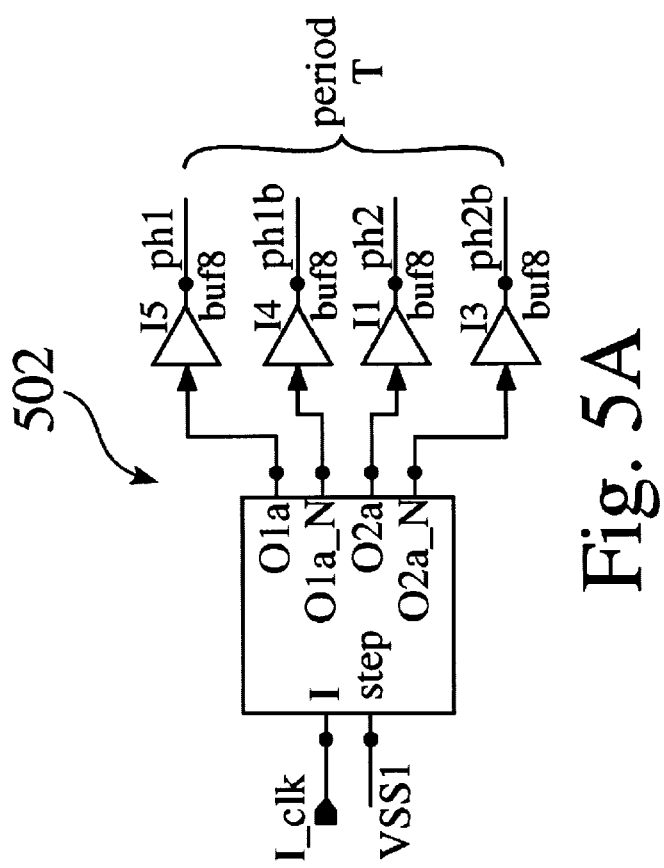
Fig. 5B
Fig. 5A

METHODS AND DEVICES FOR REDUCING INTEGRATED CIRCUIT POWER CONSUMPTION IN IMPLANTABLE CARDIAC STIMULATION DEVICES

BACKGROUND OF THE INVENTION

1. Field of the Invention

The present invention relates generally to implantable cardiac devices, such as implantable cardiac defibrillators (ICDs). The present invention more particularly relates to reducing ICD integrated circuit (IC) power consumption in such implantable cardiac devices.

2. Background Art

Implantable cardiac stimulation devices, such as implantable cardiac defibrillators (ICDs), are well known in the art. Such devices may include, for example, implantable cardiac pacemakers and defibrillators either alone or combined in a common enclosure. The devices are generally surgically implanted in a pectoral region of the chest beneath the skin of a patient. The primary components of an ICD include a monitoring and detection mechanism, a capacitor, a battery, a sensing system for detecting an arrhythmia, and a control system for controlling delivery of a capacitive discharge electrical shock in response to a detected arrhythmia. The implantable devices generally function in association with one or more electrode carrying leads which are implanted within the heart. The electrodes are positioned within the heart for making electrical contact with the muscle tissue of their respective heart chamber. Conductors within the leads couple the electrodes to the device to enable the device to deliver the desired electrical therapy.

ICDs are often employed to monitor a patient's heart to detect arrhythmias, which are irregular heartbeats that feature either very rapid ventricular contractions (tachycardia), an excessively slow heartbeat (bradychardia) or, most commonly, extra or "premature" beats. The most common arrhythmia is atrial fibrillation, which is an abnormal rhythm of the heart that can result in an increased risk of stroke due to the formation of emboli (blood clots) in the heart. More specifically, atrial fibrillation is an abnormality of heart rhythm in which chambers of the heart no longer contract in an organized manner. Heart rate often becomes irregular and may be very fast, producing palpitations. Atrial fibrillation can lead to symptoms of heart failure (shortness of breath, edema, palpitations) and chest pains and, when left untreated, occasionally can lead to stroke.

The heart has a right side and a left side. Each side has a chamber that receives blood returning to the heart (an atrium) and a muscular chamber that is responsible for pumping blood out of the heart (a ventricle). Atria are relatively thin-walled chambers, whereas the ventricles are much more muscular. Blood passes from the atria into the ventricles through two processes. During the resting phase, when the ventricles are not contracting, the tricuspid and mitral valves open. Some of the blood that has accumulated in the atria passively flows through the tricuspid and mitral valves into the right and left ventricles, respectively. The atria then contract, pumping blood out and into the ventricles. Once the ventricles fill with blood, they contract, pumping blood out of the ventricles into the lungs, and to the body.

Contractions of the different chambers of the heart are normally organized in a specific manner. An electrical impulse travels through the heart's chambers and sets off contractions. The heart's "spark plug" is a small area of specialized heart tissue called the SA node, located in the right atrium. Each time this tissue "fires," an impulse travels first through the right and left atria, signaling these chambers to contract and pump blood into the ventricles, and then'travels down into a patch of another specialized heart tissue located between the atria and the ventricles, called the AV node. Electrical-wire-like specialized tissue conducts the impulse down into the ventricles, where it signals the right ventricle to contract and to pump blood out and into the lungs, and signals the left ventricle to contract and pump blood out to the rest of the body. Normal sequence of electrical activation of the chambers of the heart is called normal sinus rhythm.

In atrial fibrillation, normal sinus rhythm does not occur. Instead, multiple "wavelets" of electrical impulses travel randomly through the atria, leading to more or less random activation of different parts of the atria at different times. Because the tissues of the right and left atria are not stimulated to contract in an organized manner, the walls of the atria more or less quiver.

Lack of organized contraction by the atria causes several detrimental things to happen. First, because less blood is pumped into the ventricles, there is less blood circulating throughout the body and blood accumulates in the lungs, causing shortness of breath (dyspnea) and other symptoms of heart failure. Second, because the heart is no longer pumping blood into the ventricles, the blood in the atria (particularly in a small part of the left atrium, the left atrial appendage) becomes relatively stagnant. There is a small but real risk that, over time, the stagnant blood will form a blood clot. If a blood clot forms, it may eventually enter the left ventricle and then get pumped out into the body. If this happens, the clot may travel to the brain, block the flow of blood in a cerebral artery, and cause a stroke.

Third, atrial fibrillation can create chest pain (angina). Multiple disorganized wavelets of electrical activity bombard the AV node with electrical impulses. When a great many electrical impulses are conducted through the AV node down into the ventricles, the ventricles contract very rapidly, producing a very fast heart rate. When the ventricles contract too rapidly, less blood is pumped into the body and blood may "back up" into the lungs. Rapid contraction increases the ventricles' demand for oxygen. The demand may exceed the ability of the coronary arteries to supply the ventricles with oxygen-rich blood, causing angina.

When an ICD detects an arrhythmia (e.g., due to atrial fibrillation), the ICD is often used to deliver an appropriate shock to the patient's heart in an attempt to return the heart to normal sinus rhythm. Sometimes, second, third, and fourth (and possibly more) shocks are required in a critical case to return the heart to normal sinus rhythm.

Current ICDs are battery powered. The battery is implanted in the patient as part of the ICD. The types of batteries used in ICDs vary. Typical ICD batteries supply voltage in the range of 2.8 to 3.6 Volts (V). As a result of on-going improvements in integrated circuit (IC) technology, however, ICs require significantly less power to operate. For example, supply voltages as low as 0.9 V are commonly used. Therefore, typical ICD batteries supply more power than is actually needed to maintain proper operation of the IC. As a result, ICD battery power is essentially wasted and the longevity of the ICD battery is reduced, requiring a patient to replace the ICD battery more frequently than is desirable. Battery replacement requires a surgical procedure. It would be desirable to minimize such surgical procedures.

Methods and devices are therefore needed to conserve ICD battery power and promote battery longevity, such that a patient will be required to undergo fewer ICD battery replacements. More generally, there is a need to reduce the amount of power an IC draws from an ICD battery.

SUMMARY OF THE INVENTION

The battery supply voltage of an implantable cardiac stimulation device (ICD) is converted to a second voltage. The second voltage is less than the battery supply voltage but sufficient for proper operation of the ICD integrated circuit (IC) or microcontroller. The current drawn from the battery is less than the current delivered to the IC.

An energy conserving step-down circuit converts the ICD battery supply voltage to the second voltage. An exemplary step-down circuit is a capacitor voltage division circuit. The step-down circuit reduces the ICD battery supply voltage according to a predetermined step-down ratio to produce the second voltage. Different embodiments of the present invention employ different step-down ratios including, for example, ratios of approximately 1:2, 1:3, 1:4, 2:3, and 3:4.

A regulator circuit regulates the second voltage to produce a regulated second voltage. An exemplary regulator circuit is a linear voltage regulator circuit. The regulator circuit stabilizes the second voltage and supplies the IC or microcontroller with a constant voltage supply. The IC or microcontroller consumes less power when supplied by the regulated second voltage than when supplied directly by the ICD battery supply voltage.

BRIEF DESCRIPTION OF THE FIGURES

Further features and advantages of the present invention may be more readily understood by reference to the following description taken in conjunction with the accompanying drawings. Like numerals or reference designators will be used to refer to like parts or elements throughout.

FIGS. 5A and 5B show an example of a step-down voltage divider circuit of the type used in this invention.

DETAILED DESCRIPTION OF THE INVENTION

The following description is of the best modes presently contemplated for practicing the invention. This description is not to be taken in a limiting sense but is made merely for the purpose of describing the general principles of the invention. The scope of the invention should be ascertained with reference to the claims.

Exemplary Stimulation Device

Figure 1:
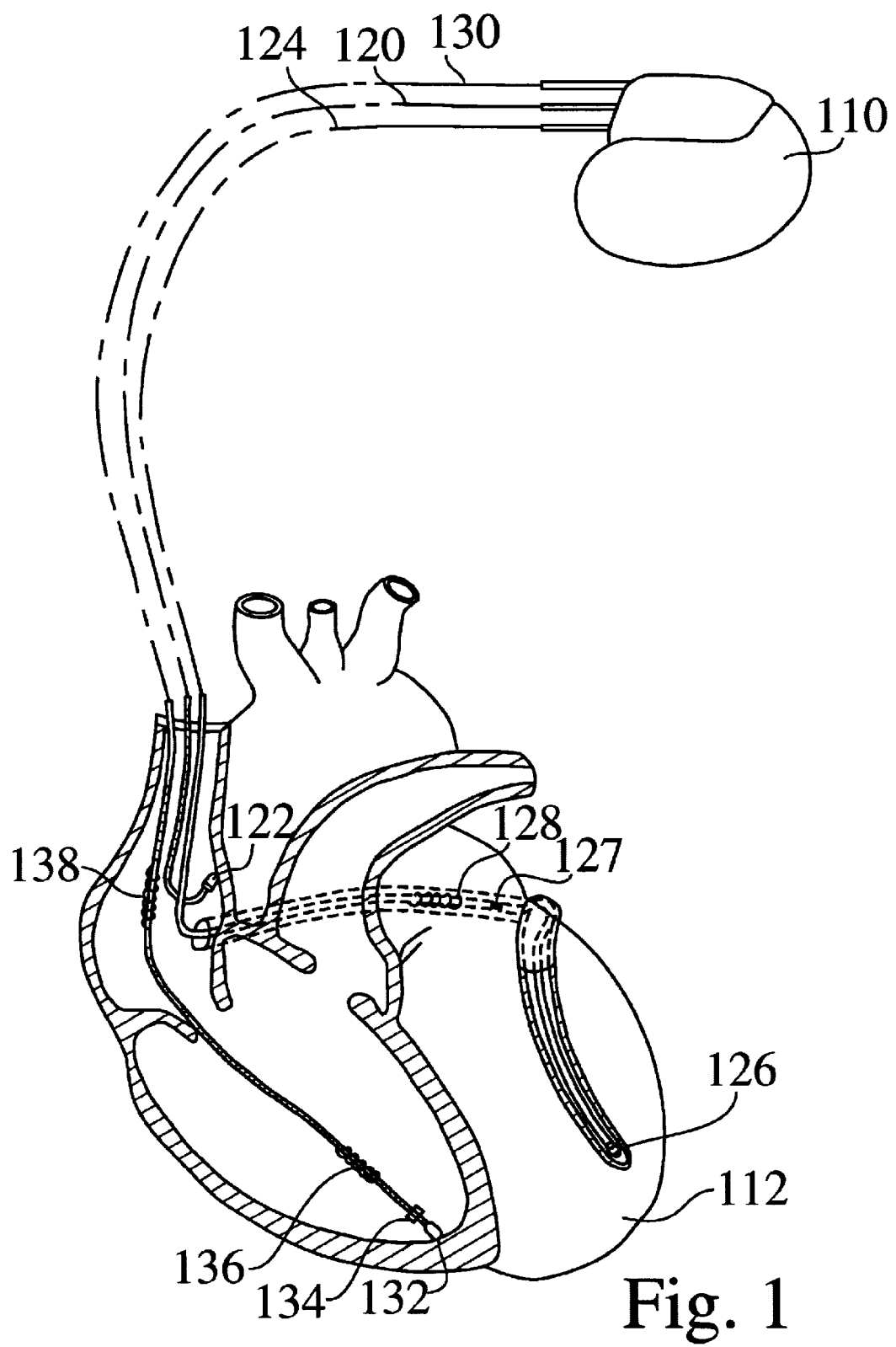
FIG. 1 is a simplified diagram illustrating an implantable stimulation device in electrical communication with at least three leads implanted into a patient's heart for delivering multi-chamber stimulation and shock therapy.

FIG. 1 shows an exemplary implantable cardiac stimulation device 110 (also referred to as a pacing device, a pacing apparatus, or an ICD) in electrical communication with a patient's heart 112 by way of three leads, 120, 124 and 130, suitable for delivering multi-chamber stimulation and shock therapy. To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage.

To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive atrial and ventricular cardiac signals and to deliver left ventricular pacing therapy using at least a left ventricular tip electrode 126, left atrial pacing therapy using at least a left atrial ring electrode 127, and shocking therapy using at least a left atrial coil electrode 128.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle.

Figure 2:
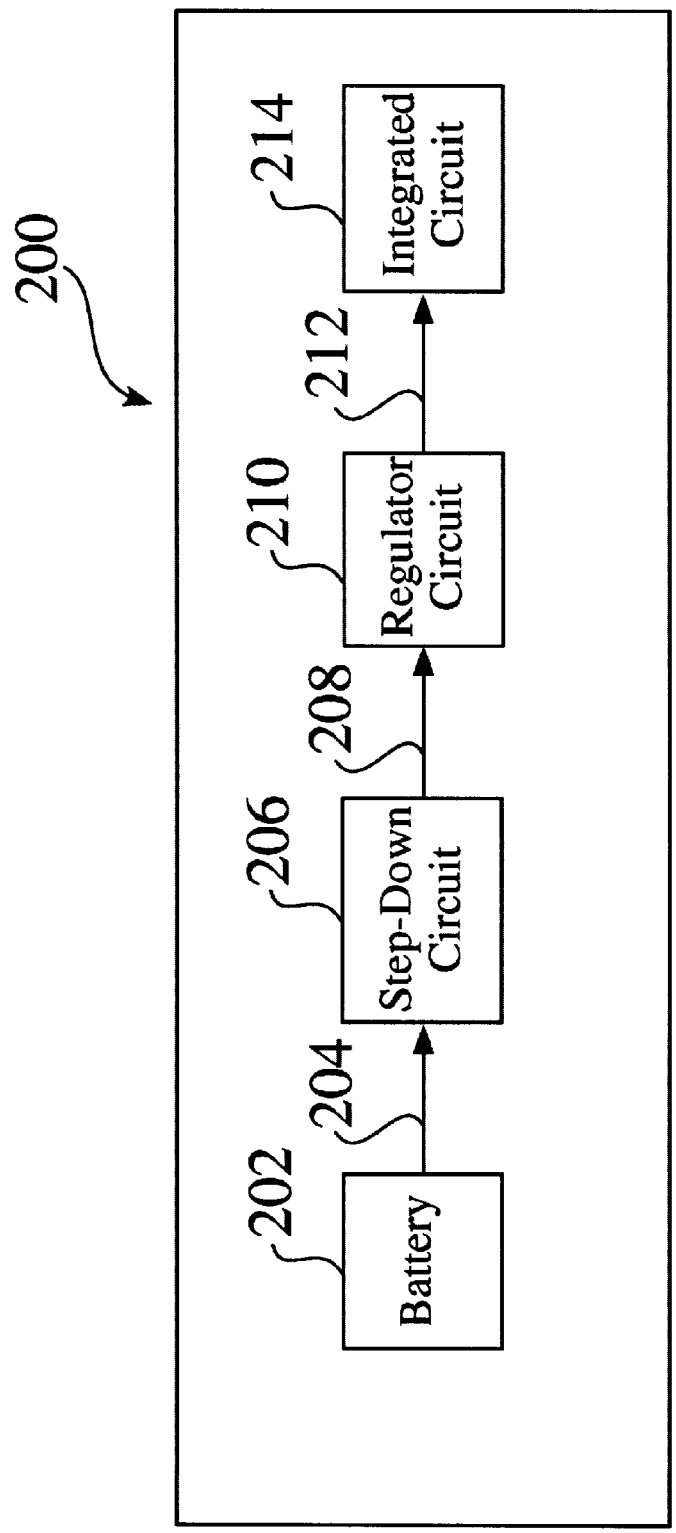
FIG. 2 is a block diagram of the voltage step-down circuit elements of this invention.

FIG. 2 is a block diagram of the step-down voltage circuit elements which comprise the present invention. The circuit elements include a battery 202, a step-down circuit 206, a regulator circuit 210, and an integrated circuit (IC) or microcontroller 214. Battery 202 produces a battery supply voltage 204. A second voltage 208 is regulated by voltage regulator circuit 210 to produce a regulated second voltage 212. Regulator circuit 210 stabilizes second voltage 208 to remove fluctuations in battery supply voltage 204 and supplies IC 214 with regulated second voltage 208.

The type of battery used in ICD 110 varies but typical ICD batteries 202 produce battery supply voltages 204 in the range of 2.8 to 3.6 Volts (V). A typical IC 214 requires significantly less power to operate than 2.8 to 3.6 V. For example, supply voltages as low as 0.9 V are commonly used.

To reduce wastage of battery power and extend battery life, the present invention incorporates an energy conserving voltage step-down circuit 206 to reduce the battery supply voltage 204. Step-down circuit 206 is a capacitor voltage division circuit implemented with transistors configured to function as switches. The number of capacitors and switching sequences of the transistors determine the step-down ratio, or the amount by which battery supply voltage 204 will be reduced to produce a second voltage 208 which is less than the battery supply voltage 204 but sufficient to maintain proper operation of the IC or microcontroller 214. The step-down circuit reduces the current consumption delivered to the IC by an amount which is a function of the step down ratio of the step-down circuit. Battery supply voltage 204 is reduced according to a predetermined step-down ratio with negligible power loss. Typical predetermined step-down ratios include ratios of approximately 1:2, 1:3, 1:4, 2:3, and 3:4. One skilled in the art will recognize that the present invention is not limited to the aforementioned step-down ratio values.

Figure 3:
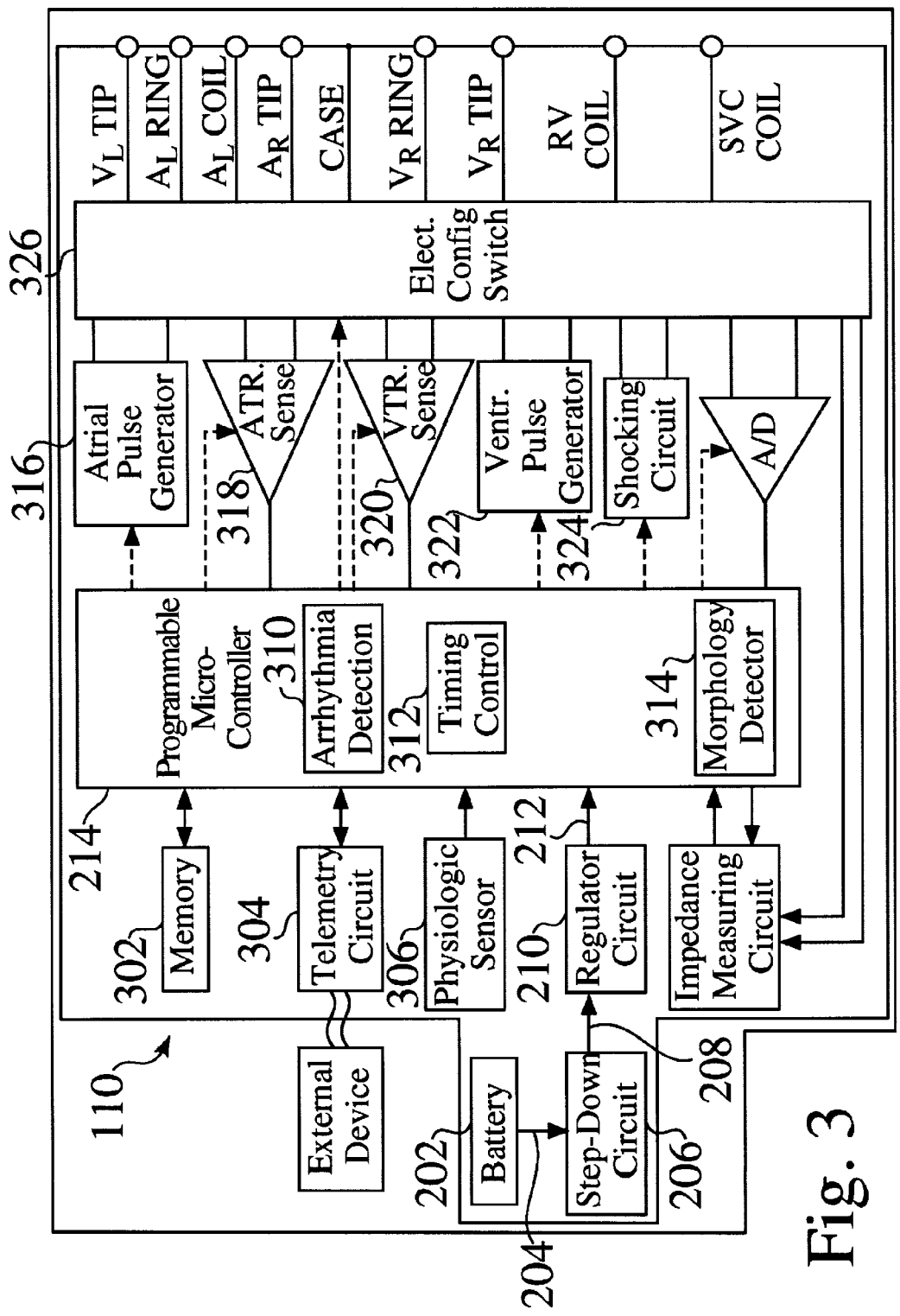
FIG. 3 is an illustration of the elements of the present invention in a functional block diagram of a multi-chamber implantable stimulation device.

FIG. 3 is a simplified block diagram of an exemplary multi-chamber implantable cardiac stimulation device 110 which incorporates the present invention. Stimulation device 110 is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. Additional details of stimulation device 110 are disclosed in co-pending, commonly assigned application Ser. No. 09/861,230, filed May 17, 2001 in the name of Mark W. Kroll, titled "METHODS AND DEVICES FOR RAPID DELIVERY OF SECONDARY CARDIAC SHOCKS," the disclosure of which is incorporated herein by reference.

As further shown in FIG. 3, microcontroller 214 typically includes a microprocessor, or equivalent control circuitry, designed specifically for controlling the delivery of stimulation therapy. The details of the design of microcontroller 214 are not critical to the present invention. The use of microprocessor-based control circuits for performing timing and data analysis functions is well known in the art.

Microcontroller 214 includes timing control circuitry 312 which is used to control pacing parameters. Microcontroller 214 classifies the timing intervals by comparing them to predefined limits and various other characteristics (e.g., physiologic sensors 306, morphology detector 314, etc.) in order to determine the type of remedial therapy that is needed (e.g., pacing, defibrillation shocks). A sensing system of the present invention, for example, is implemented in the arrhythmia detection software and/or hardware 310 of microcontroller 214. Each sensing circuit 318 and 320 in device 110, preferably employs one or more low power, precision amplifiers with programmable gain and/or automatic gain control, bandpass filtering, and a threshold detection circuit, as known in the art, to selectively sense the cardiac signal of interest.

As further shown in FIG. 3, microcontroller 214 controls pulse generators 316 and 322 via appropriate control signals to trigger or inhibit stimulation pulses and further controls a shocking circuit 324. Microcontroller 214 is also coupled to a memory 302, wherein the programmable operating parameters used by the microcontroller 214 are stored and modified, as required, in order to customize the operation of stimulation device 110 to suit the needs of a particular patient. Advantageously, the operating parameters of the implantable device 110 may be non-invasively programmed into memory 302 through a telemetry circuit 304.

The stimulation device 110 additionally includes battery 202 which provides operating power to all of the circuits shown in FIG. 2. Accordingly, stimulation device 110 preferably employs lithium silver vanadium oxide batteries. However, many other types of batteries can be used, such as a lithium titanium disulfide battery, without departing from the spirit and scope of the present invention. Also shown in FIG. 3 is step-down circuit 206 that reduces battery supply voltage 204, and regulator circuit 210 that stabilizes second voltage 208 and supplies regulated second voltage 212 to microcontroller 214.

Figure 4:
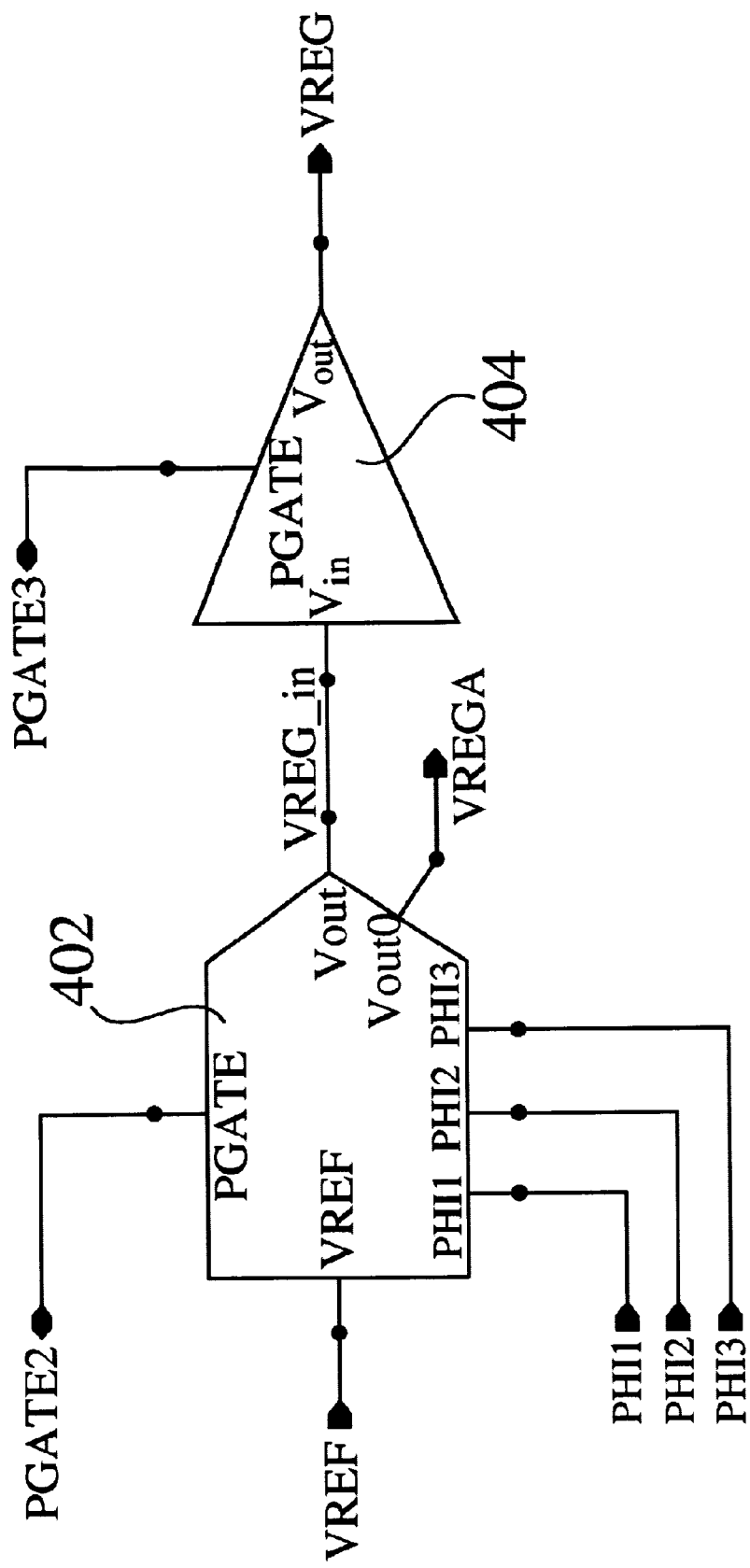
FIG. 4 is a schematic of an exemplary linear voltage regulator circuit that can be used in an embodiment of the present invention.

FIG. 4 is a schematic of an exemplary linear voltage regulator circuit 210 that can be used in an embodiment of the present invention. Regulator 210 comprises a voltage reference amplifier 402 and a buffer 404 that generates the regulated and stabilized voltage. Amplifier 402 receives second voltage 208 from step-down circuit 206 and a reference voltage at input $V_{REF}$. Amplifier 402 produces the stabilized voltage at output $V_{out}$. Buffer 404 regulates the second voltage 208 and generates sufficient current at the desired stabilized voltage to power the circuit components of IC 214. Regulator 210 supplies the IC 214 with the regulated second voltage 212 at output $V_{REG}$ of buffer 404, providing a constant desired voltage supply despite any fluctuations that may be present in the second voltage 208. The PGATE inputs to amplifier 402 and buffer 404 are reference current inputs generated elsewhere in the circuit. The PHI inputs to amplifier 402 are clock phase inputs FIGS. 5A and 5B show an example of a step-down voltage divider circuit of the type used in this invention. FIG. 5A shows a non-overlapping clock generator circuit 502. The clock generator circuit has an input I_clk which is typically a 1–2 kHz clock signal. Circuit 502 has four outputs: ph1, ph1$b$, ph2 and ph2$b$. Output ph1$b$ is the inverted output of ph1; and output ph2$b$ is the inverted output of ph2. Outputs ph1 and ph2 are non-overlapping. They are guaranteed not to be high at the same time. Similarly, outputs ph1$b$ and ph2$b$ are non-overlapping.

Outputs ph1, ph1$b$, ph2 and ph2$b$ drive a step down circuit 504 shown in FIG. 5B. Circuit 504 comprises a plurality of transistor switches. In the example shown, there are six transistor switches, labeled as 506$a$–$f$, respectively. A pair of capacitors $C_1$ and $C_2$ are coupled across the outputs of step-down circuit 504. Capacitor $C_1$ is denoted as the step-down capacitor. Capacitor $C_2$ is denoted as the reservoir capacitor. In the example shown, capacitor $C_1$ has a value of 10Φf; and capacitor $C_2$ has a value of 10Φf. As shown, the step down voltage divider reduces the input voltage by one-half. Thus the output voltage V_divider is one half the value of input voltage VDD. It would be apparent to those skilled in the art that modifications to the circuit arrangement shown could be made to produce different integer divisions of the input voltage.

The above description provides examples of regulator and step-down circuits that can be used with the present invention. Those skilled in the relevant art will appreciate that other voltage regulator and voltage step-down circuits can be used while still being within the spirit and scope of the present invention.

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

What is claimed is:

1. A method for reducing power consumption by an integrated circuit in an implantable cardiac stimulation device, comprising the steps of:
   a. converting a battery supply voltage to a second voltage, said second voltage being less than said battery supply voltage but sufficient for proper operation of the integrated circuit;
   b. regulating said second voltage to produce a regulated second voltage; and c. providing said regulated second voltage to the integrated circuit, whereby power consumption of the integrated circuit when supplied by said regulated second voltage is less than power consumption of the integrated circuit when supplied directly by the battery supply voltage.

2. The method of claim 1, wherein step (a) comprises the step of reducing the battery supply voltage in an amount according to a predetermined step-down ratio.

3. The method of claim 2, wherein said predetermined step-down ratio is approximately 1:2.

4. The method of claim 2, wherein said predetermined step-down ratio is approximately 1:3.

5. The method of claim 2, wherein said predetermined step-down ratio is approximately 1:4.

6. The method of claim 2, wherein said predetermined step-down ratio is approximately 2:3.

7. The method of claim 2, wherein said predetermined step-down ratio is approximately 3:4.

8. The method of claim 1, wherein step (b) comprises the step of stabilizing said second voltage to provide a constant voltage to said integrated circuit.

9. An apparatus for reducing power consumption by an integrated circuit in an implantable cardiac stimulation device, comprising:

a step-down circuit for converting a battery supply voltage to a second voltage, said second voltage being less than said battery supply voltage but sufficient for proper operation of the integrated circuit; and a regulator for regulating said second voltage to produce a regulated second voltage and providing said regulated second voltage to the integrated circuit, whereby power consumption of the integrated circuit when supplied by said regulated second voltage is less than power consumption of the integrated circuit when supplied directly by the battery supply voltage.

10. The apparatus of claim 9, whereby said step-down circuit reduces said battery supply voltage according to a predetermined step-down ratio.

11. The apparatus of claim 10, wherein said predetermined step-down ratio is approximately 1:2.

12. The apparatus of claim 10, wherein said predetermined step-down ratio is approximately 1:3.

13. The apparatus of claim 10, wherein said predetermined step-down ratio is approximately 1:4.

14. The apparatus of claim 10, wherein said predetermined step-down ratio is approximately 2:3.

15. The apparatus of claim 10, wherein said predetermined step-down ratio is approximately 3:4.

16. The apparatus of claim 9, wherein said step-down circuit is a capacitor voltage division circuit.

17. The apparatus of claim 9, wherein said regulator is linear voltage regulator circuit.

18. The apparatus of claim 9, whereby said regulator stabilizes said second voltage to provide a constant voltage to said integrated circuit.

19. The apparatus of claim 9, wherein said integrated circuit is a programmable microcontroller.

20. An implantable cardiac stimulation device comprising:

a programmable microcontroller;

a battery; and means for stepping-down a voltage supplied by said battery to a second voltage, said second voltage being less than said voltage supplied by said battery but sufficient for proper operation of said microcontroller, whereby power consumption of the microcontroller when supplied by said second voltage is less than power consumption of the microcontroller when supplied directly by said battery.

21. The device of claim 20, wherein said stepping-down means comprises:

a step-down circuit coupled to said battery for converting a voltage supplied by said battery to said second voltage; and a regulator coupled to and between said step-down circuit and said microcontroller for regulating said second voltage to produce a regulated second voltage and providing said regulated second voltage to the microcontroller.

22. The device of claim 21, whereby said step-down circuit reduces said voltage supplied by said battery according to a predetermined step-down ratio.

23. The device of claim 22, wherein said predetermined step-down ratio is approximately 1:2.

24. The device of claim 22, wherein said predetermined step-down ratio is approximately 1:3.

25. The device of claim 22, wherein said predetermined step-down ratio is approximately 1:4.

26. The device of claim 22, wherein said predetermined step-down ratio is approximately 2:3.

27. The device of claim 22, wherein said predetermined step-down ratio is approximately 3:4.

28. The device of claim 21, wherein said step-down circuit is a capacitor voltage division circuit.

29. The device of claim 21, wherein said regulator is a linear voltage regulator circuit.

30. The device of claim 21, whereby said regulator stabilizes said second voltage to provide a constant voltage to said microcontroller.

* * * * *